United States Patent
Knight

(10) Patent No.: US 10,874,822 B2
(45) Date of Patent: Dec. 29, 2020

(54) AIRCRAFT SEAT ASSEMBLY INCLUDING A VIBRATION PRODUCING APPARATUS AND METHOD FOR FABRICATING THE SAME

(71) Applicant: Gulfstream Aerospace Corporation, Savannah, GA (US)

(72) Inventor: Michael Knight, Savannah, GA (US)

(73) Assignee: Gulfstream Aerospace Corporation, Savannah, GA (US)

( * ) Notice: Subject to any disclaimer, the term of this patent is extended or adjusted under 35 U.S.C. 154(b) by 98 days.

(21) Appl. No.: 16/197,847

(22) Filed: Nov. 21, 2018

(65) Prior Publication Data

US 2020/0155792 A1    May 21, 2020

(51) Int. Cl.
| | | |
|---|---|---|
| *A61M 21/02* | (2006.01) | |
| *B64D 11/06* | (2006.01) | |
| *A61H 23/02* | (2006.01) | |
| *A61M 21/00* | (2006.01) | |
| *B60N 2/90* | (2018.01) | |
| *H04R 1/02* | (2006.01) | |

(52) U.S. Cl.
CPC ......... *A61M 21/02* (2013.01); *A61H 23/0263* (2013.01); *B60N 2/976* (2018.02); *B64D 11/06* (2013.01); *H04R 1/025* (2013.01); *A61H 2201/0149* (2013.01); *A61H 2201/1238* (2013.01); *A61H 2201/1623* (2013.01); *A61H 2201/5007* (2013.01); *A61H 2201/5025* (2013.01); *A61H 2203/0431* (2013.01); *A61M 2021/0022* (2013.01); *H04R 2499/13* (2013.01)

(58) Field of Classification Search
CPC ............. A61M 21/00–02; B60N 2/976; A61H 2201/0149; A61H 23/0236; B64D 11/06
See application file for complete search history.

(56) References Cited

U.S. PATENT DOCUMENTS

| | | | | |
|---|---|---|---|---|
| 5,669,818 A * | 9/1997 | Thorner | .................. | A63F 13/02 463/30 |
| 5,845,236 A * | 12/1998 | Jolly | ................ | G10K 11/17861 702/195 |
| 6,053,880 A * | 4/2000 | Sleichter, III | ............ | A47C 7/40 297/217.3 |
| 2004/0201481 A1* | 10/2004 | Yoshinori | ................ | B60N 2/56 340/575 |
| 2008/0309132 A1* | 12/2008 | Katsuta | .................. | A61H 23/02 297/217.3 |
| 2010/0139870 A1* | 6/2010 | Ochoa | .................... | B60C 25/04 157/1.17 |

(Continued)

OTHER PUBLICATIONS

Amzar Azizan, et al., The Influence of Vibration on Seated Human Drowsiness, Article, Industrial Health 2016, 54, 296-307, Jan. 30, 2016.

*Primary Examiner* — Thaddeus B Cox
(74) *Attorney, Agent, or Firm* — LKGlobal | Lorenz & Kopf, LLP

(57) ABSTRACT

An aircraft seat assembly for supporting a seat occupant, and a method for fabricating an aircraft seat assembly for supporting a seat occupant are provided. In one non-limiting example, the aircraft seat assembly includes a seat cushion supported by the seat structure. A vibration producing apparatus configured to produce vibrations conducive for inducing drowsiness. The vibration producing apparatus is disposed adjacent to or within the seat structure for transferring the vibrations to the seat occupant.

12 Claims, 4 Drawing Sheets

(56) References Cited

U.S. PATENT DOCUMENTS

| | | | |
|---|---|---|---|
| 2012/0226418 A1* | 9/2012 | Veen | B60N 2/0276 |
| | | | 701/49 |
| 2015/0202991 A1* | 7/2015 | Sugiyama | A61M 21/00 |
| | | | 340/575 |
| 2018/0065517 A1* | 3/2018 | Kuhley | B60N 2/976 |
| 2018/0140798 A1* | 5/2018 | Tomiyama | A61M 21/02 |
| 2020/0054518 A1* | 2/2020 | Noso | A61H 9/0078 |

* cited by examiner

US 10,874,822 B2

AIRCRAFT SEAT ASSEMBLY INCLUDING A VIBRATION PRODUCING APPARATUS AND METHOD FOR FABRICATING THE SAME

TECHNICAL FIELD

The technical field relates generally to aircraft seat assemblies, and more particularly, relates to aircraft seat assemblies including a vibration producing apparatus configured to produce vibrations for transfer to a seat occupant, the vibrations being conducive for inducing drowsiness, and methods for fabricating such aircraft seat assemblies.

BACKGROUND

The commercial and/or military transportation industries, e.g., aircraft industry, often include aircraft seat assemblies in the aircraft for comfortably transporting a passenger(s) and/or other vehicle occupant(s). The aircraft seat assemblies include, for example, a seat frame that supports a plurality of seat cushions, such as a seat base cushion and a seat backrest cushion, for providing comfortable seating for an occupant.

During relatively long trips, such as long-range flights or the like, passengers may want to sleep. To help, for example, flight attendants may turn down the lights and keep the cabin area relatively quiet, while some passengers may reorient their seat by reclining the seat backrest portion, close the adjacent window shade, and use a pillow and/or blanket for additional comfort. Despite these efforts, unfortunately some passengers are not as successful as others in becoming drowsy and falling sleeping.

Accordingly, it is desirable to provide improved aircraft seat assemblies that can help seat occupants who wish to sleep to become drowsy and fall asleep, and methods for fabricating such aircraft seat assemblies. Furthermore, other desirable features and characteristics of the various embodiments described herein will become apparent from the subsequent detailed description and the appended claims, taken in conjunction with the accompanying drawings and this background.

SUMMARY

Various non-limiting embodiments of an aircraft seat assembly for supporting a seat occupant, and various non-limiting embodiments of a method for fabricating an aircraft seat assembly for supporting a seat occupant, are provided herein.

In a first non-limiting embodiment, the aircraft seat assembly includes, but is not limited to, a seat structure. The aircraft seat assembly further includes, but is not limited to, a seat cushion supported by the seat structure. The aircraft seat assembly further includes, but is not limited to, a vibration producing apparatus configured to produce vibrations. The vibration producing apparatus is disposed one of adjacent to and within the seat structure for transferring the vibrations to the seat occupant.

In another non-limiting embodiment, the aircraft seat assembly includes, but is not limited to, a seat base portion that includes a seat base structure portion and a seat base cushion supported by the seat base structure portion. The aircraft seat assembly further includes, but is not limited to, a seat backrest portion that is coupled to the seat base portion. The seat backrest portion is configured to extend substantially upright from the seat base portion. The seat backrest portion further includes a seat backrest structure portion and a seat backrest cushion that is supported by the seat backrest structure portion. The aircraft seat assembly further includes, but is not limited to, a vibration producing apparatus that is configured to produce vibrations. The vibration producing apparatus is disposed one of adjacent to and within one of the seat base structure portion and the seat backrest structure portion for transferring the vibrations to the seat occupant.

In another non-limiting embodiment, the method includes, but is not limited to, the step of supporting a seat cushion by a seat structure. The method further includes, but is not limited to, the step of incorporating a vibration producing apparatus into the aircraft seat assembly. The vibration producing apparatus is configured for producing vibrations. The step of incorporating the vibration producing apparatus includes disposing the vibration producing apparatus one of adjacent to and within the seat structure for transferring the vibrations to the seat occupant.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following Detailed Description is merely exemplary in nature and is not intended to limit the various embodiments or the application and uses thereof. Furthermore, there is no intention to be bound by any theory presented in the preceding background or the following detailed description.

Various embodiments contemplated herein relate to aircraft seat assemblies and methods for fabricating aircraft seat assemblies for an aircraft. The exemplary embodiments taught herein provide an aircraft seat assembly that includes a seat structure and a seat cushion that is supported by the seat structure. The aircraft seat assembly further includes a vibration producing apparatus that is configured to produce vibrations. The vibration producing apparatus is disposed adjacent to and/or within the seat structure for transferring the vibrations to the seat occupant, e.g., passenger of the aircraft. In an exemplary embodiment, the vibrations produced by the vibration producing apparatus are relatively low frequency vibrations that are conducive for inducing drowsiness.

In an exemplary embodiment, the aircraft seat assembly further includes a control panel and a controller that is in communication with both the control panel and the vibration producing apparatus. When the seat occupant would like to fall asleep, the occupant can provide an input to the control panel, for example by actuating a button, knob, or the like that is arranged on the control panel. In response, the control panel generates an input signal that is transmitted to the controller. The controller receives the input signal and generates a command signal in response to the input signal. The command signal provides instructions to the vibration producing apparatus to produce the vibrations in the aircraft seat assembly to help the seat occupant to become drowsy and fall asleep.

Figure 1:
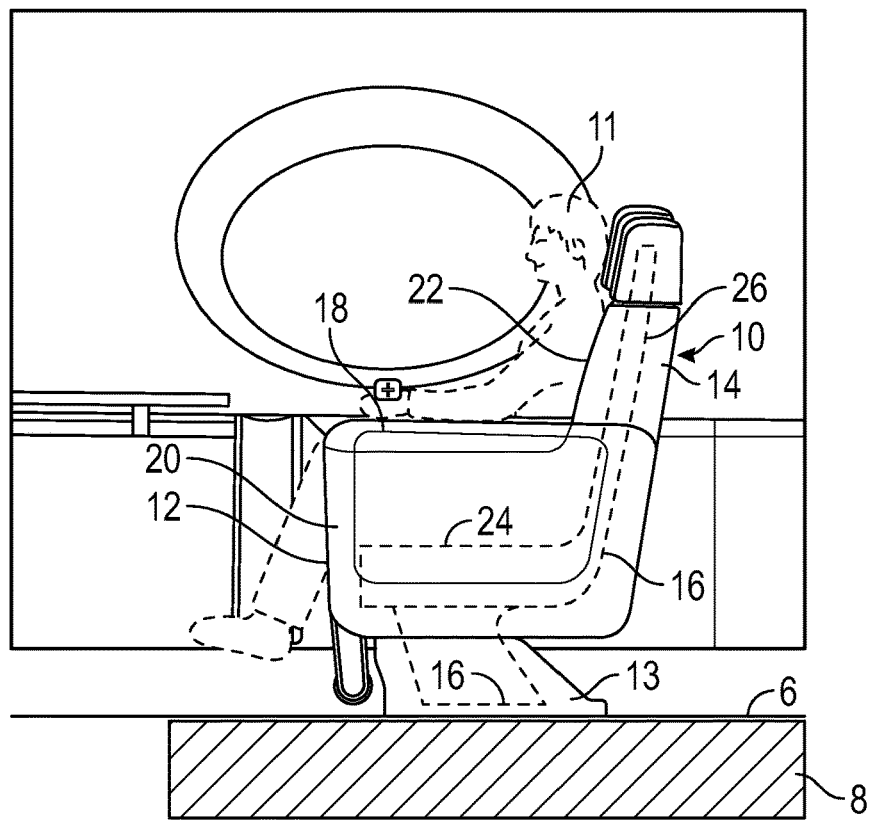
FIG. 1 illustrates a side view of an aircraft seat assembly supporting a seat occupant in accordance with an exemplary embodiment.

FIG. 1 illustrates a side view of an aircraft seat assembly 10 supporting a seat occupant 11 in accordance with an exemplary embodiment. As illustrated, a lower portion of the aircraft seat assembly 10 is coupled to a seat track 6 that is supported on a vehicle structure, e.g., airframe structure of the aircraft or the like.

The aircraft seat assembly 10 has a seat base portion 12 that includes a seat substructure 13, and a seat backrest portion 14 that extends substantially upright from the seat base portion 12. In one example, the seat backrest portion 14 is fixedly coupled to the seat base portion 12 such that the seat backrest portion 14 is permanently set in a substantially upright configuration. In another example, the aircraft seat assembly 10 is an adjustable aircraft seat assembly in which the seat backrest portion 14 is pivotably coupled to the seat base portion 12 for movement between a substantially upright position and, for example, a substantially reclined (e.g., rearward leaning) position.

As illustrated, the aircraft seat assembly 10 includes a seat frame 16 (also referred to herein as "seat structure") for supporting the aircraft seat assembly 10 including supporting armrest portions 18 and a plurality of seat cushions 20 and 22. The seat frame 16 is formed of a relatively rigid support material such as metal, e.g., aluminum or the like, composite, or any other frame structure material(s) known to those skilled in the art.

The seat frame 16 includes a seat base structure portion 24 and a seat backrest structure portion 26 that is operatively coupled (e.g., fixedly coupled or pivotably coupled) to the seat base structure portion 24 to extend in a substantially upright position from the seat base structure portion 24. The seat base structure portion 24 of the seat frame 16 supports a seat base cushion 20 that together form at least part of the seat base portion 12 of the aircraft seat assembly 10. Likewise, the seat backrest structure portion 26 of the seat frame 16 supports a seat backrest cushion 22 that together form at least part of the seat backrest portion 14 of the aircraft seat assembly 10. Various other trim and/or shell panels or components may be directly or indirectly coupled to the seat frame 16 to form any remaining parts or sections of the seat base portion 12 and/or the seat backrest portion 14 of the aircraft seat assembly 10.

The seat base and backrest cushions 20 and 22 are each formed of relatively flexible and/or soft materials such as a foam material(s) that is covered or at least partially covered with an outer covering. The outer covering is a relatively flexible and/or soft skin material such as leather, cloth or textile fabric (e.g., woven or knitted construction), thermoplastic skin material such as TPO, PVC, or the like. The outer covering may be formed using a conventional leather forming process, a thermoforming process, a slush or rotational molding process, and/or any other conventional process for forming an interior trim outer skin covering that is relatively flexible and/or soft.

Figure 2:
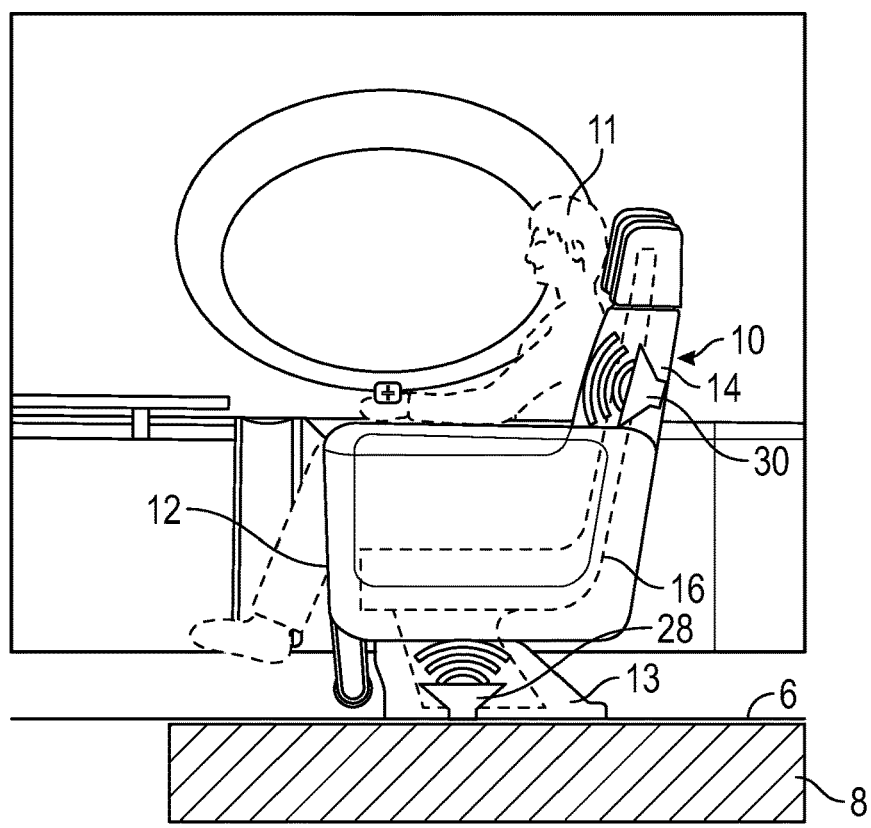
FIG. 2 illustrates a side view of an aircraft seat assembly including a vibration producing apparatus and a seat occupant in accordance with an exemplary embodiment.

Referring to FIG. 2, the aircraft seat assembly 10 includes one or more a vibration producing apparatuses 28 and 30 each configured to produce vibrations conducive for inducing drowsiness. Although the aircraft seat assembly 10 is illustrated as having two vibration producing apparatuses 28 and 30, it is to be understood that various embodiments may include a single vibration producing apparatus or alternatively, may include more than two vibration producing apparatuses.

In an exemplary embodiment, each of the vibration producing apparatuses 28 and 30 are configured to produce relatively low frequency vibrations having a frequency of from about 1 to about 15 Hz, and an amplitude of from about 0.005 inches to about 1 inch for inducing drowsiness. In an exemplary embodiment, the vibration producing apparatuses 28 and/or 30 are configured to produce relatively smooth, sinusoidal waveforms. In an alternative embodiment, the vibration producing apparatuses 28 and/or 30 are configured to produce triangular waveforms.

In an exemplary embodiment, the vibration producing apparatuses 28 and 30 are arranged adjacent to and/or within the seat frame 16 (e.g., seat structure) for transferring the vibrations to the seat occupant 11. As illustrated, the vibration producing apparatus 28 is disposed adjacent to and/or within the seat base structure portion 24, specifically of the seat substructure 13 of the seat base portion 12, and the vibration producing apparatus 30 is disposed adjacent to and/or within the seat backrest structure portion 26 of the seat backrest portion 14 to direct or otherwise transfer the vibrations towards the seat occupant 11.

Figure 3:
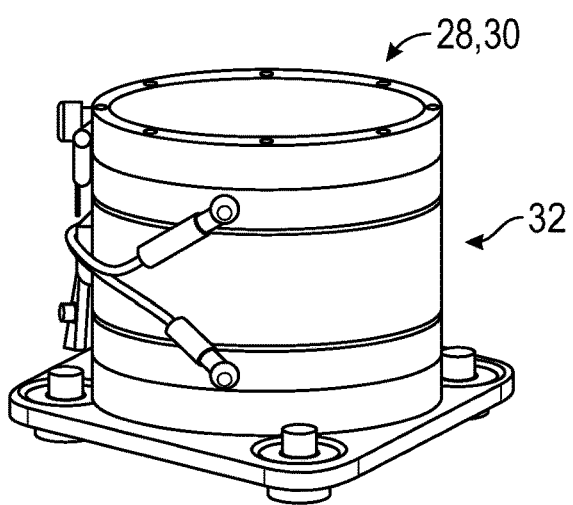
FIG. 3 illustrates a perspective view of a vibration producing apparatus in accordance with an exemplary embodiment.
Figure 4:
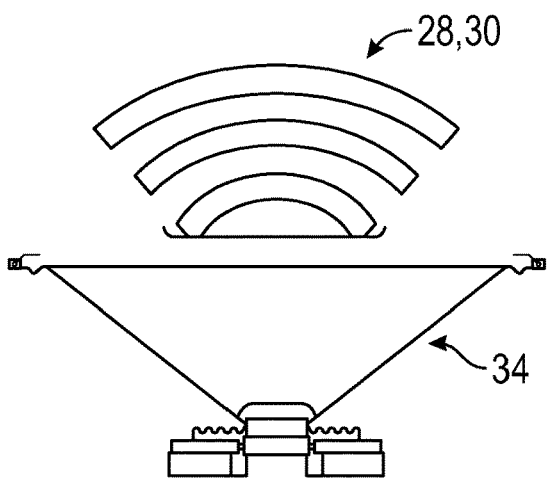
FIG. 4 illustrates a side view of a vibration producing apparatus in accordance with an exemplary embodiment.

As will be discussed in further detail below, in an exemplary embodiment, the vibration producing apparatuses 28 and 30, independently, can be an audio speaker, a shaker actuator, a motorized eccentric shaker, or a pneumatic mechanism device. Referring to also FIGS. 3-4, in an exemplary embodiment, the vibration producing apparatuses 28 and 30, independently, are a shaker actuator 32 or an audio speaker 34. Without being limited by theory, in an exemplary embodiment, both the shaker actuator 32 and the audio speaker 34 function in similar ways, using a magnet(s) and coils to produce a small displacement at a controlled frequency. The audio speaker 34 imparts the vibration energy to air within the aircraft seat assembly 10 to produce sound while the shaker actuator 32 has an internal "stinger" (e.g., a rod that impacts a membrane, for example like a drum head, to produce vibrations) that acts like a small battering ram to transfer energy into the aircraft seat assembly 10. Both the shaker actuator 32 and the audio speaker 34 are configured to produce vibrations at the desired frequency and amplitude for inducing drowsiness.

Figure 5:
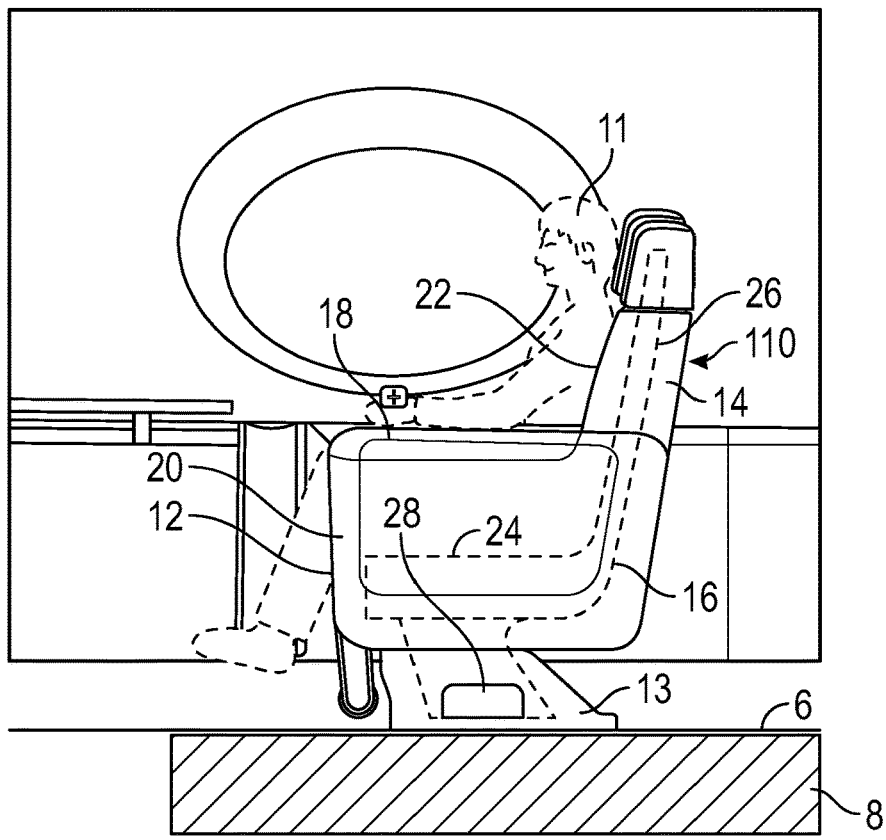
FIG. 5 illustrates a side view of an aircraft seat assembly including a vibration producing apparatus and a seat occupant in accordance with another exemplary embodiment.

FIG. 5 illustrates a side view of an aircraft seat assembly 110 supporting a seat occupant 11 in accordance with an exemplary embodiment. The aircraft seat assembly 110 is similarly configured to the aircraft seat assembly 10 as previously discussed in relationship to FIG. 2 including the seat base portion 12 including the seat substructure 13, the seat backrest portion 14, the seat frame 16, the armrest portion 18, the seat base cushion 20, the seat backrest cushion 22, the seat base structure portion 24, and the seat backrest structure portion 26, but with the exception that the aircraft seat assembly 110 is shown as having only a single vibration producing apparatus 28. As illustrated, the vibration producing apparatus 28 is disposed adjacent to and/or within the seat base structure portion 24, specifically of the seat substructure 13 of the seat base portion 12 and is configured to produce vibrations conducive for inducing drowsiness as discussed above.

Figure 6:
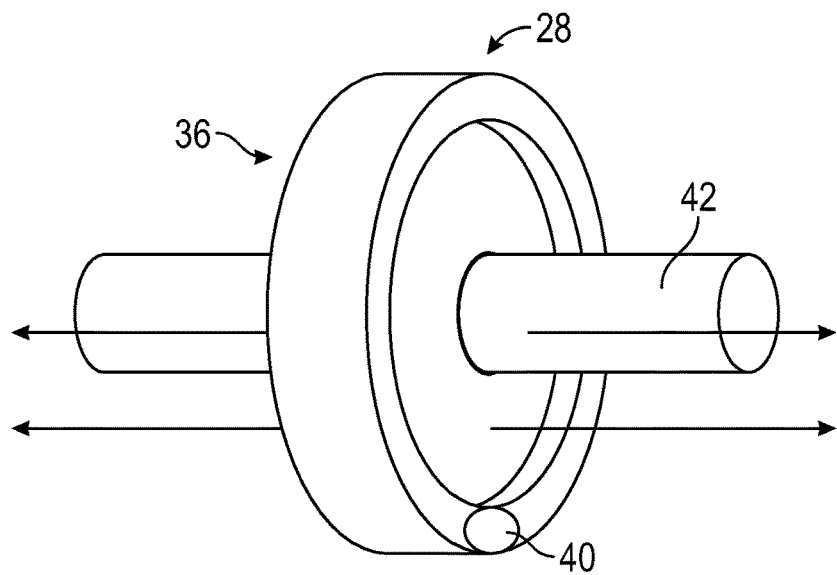
FIG. 6 illustrates a perspective view of a vibration producing apparatus in accordance with an exemplary embodiment.
Figure 7:
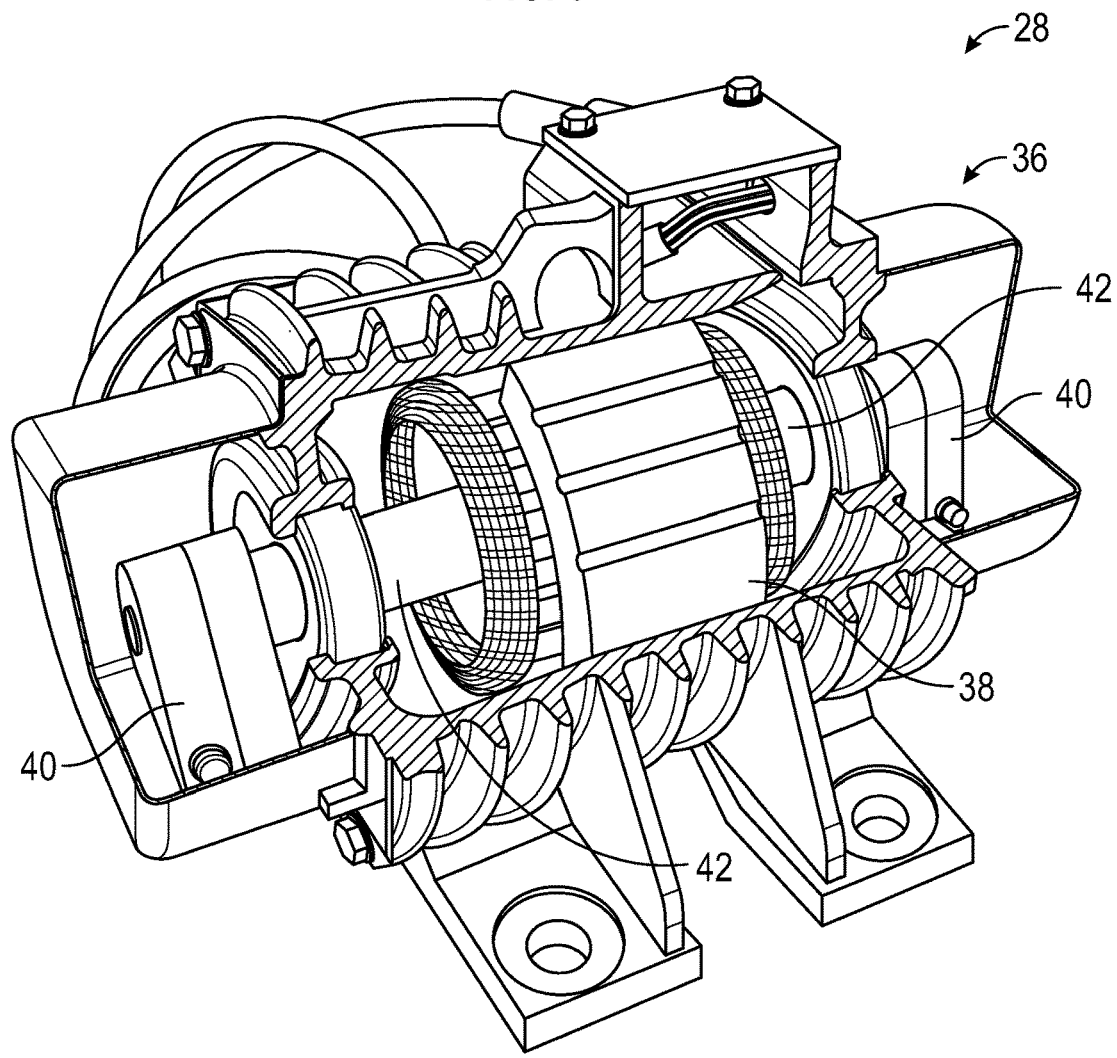
FIG. 7 illustrates a tear-away perspective view of a vibration producing apparatus in accordance with an exemplary embodiment.

Referring also to FIGS. 6-7, in an exemplary embodiment, the vibration producing apparatus 28 is a motorized eccentric shaker 36. In one example, the motorized eccentric shaker 36 is configured to produce relatively smooth sinusoidal vibrations at a relatively low frequency conducive for inducing drowsiness. The motorized eccentric shaker 36 includes a motor 38 (e.g., electric motor) with one or more offset weights 40 attached to a motor shaft 42. In particular, the mass of the offset weight 40 is off-center of the rotation of the motor shaft 42. The frequency produced by the motorized eccentric shaker 36 can be varied by changing the motor voltage being supplied to the motor 38, thereby changing the rotational speed of the motor 38. Further, the amplitude of the vibrations can be varied by moving the offset weights closer or further away from the motor shaft 42.

Figure 8:
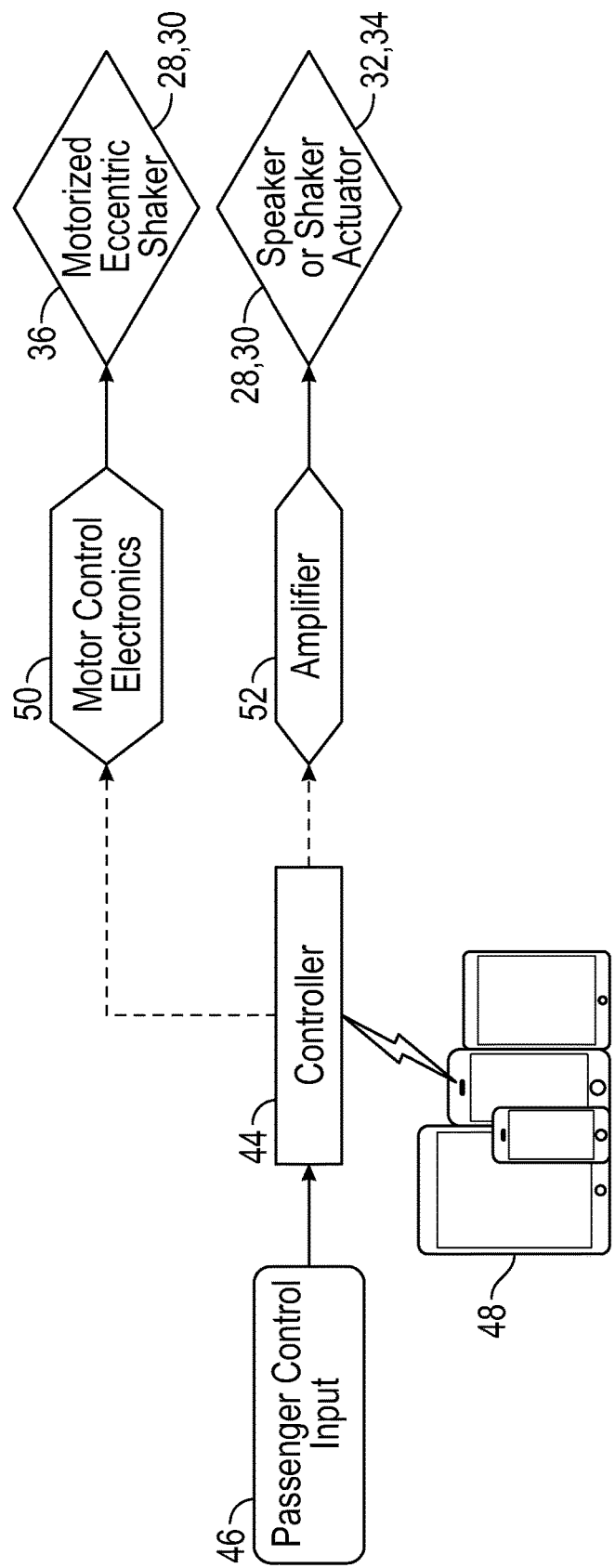
FIG. 8 illustrates a schematic representation of a vibration producing apparatus in accordance with an exemplary embodiment.

Referring to FIG. 8, a schematic representation of the vibration producing apparatuses 28 and/or 30 in communication with a controller 44, a control panel 46, an onboard network or a mobile device 48, motor control electronics 50, and an amplifier 52 is provided. In an exemplary embodiment, the controller 44 is configured to receive an input signal. In one example, an input is provided by the seat occupant (e.g., the seat occupant can vary the frequency and amplitude settings to their preference) to the control panel that in response, generates the input signal that is communicated to the controller 44. In another example, an input is provided to the onboard network or the mobile device 48 that in response, generates the input signal that is communicated to the controller 44.

The controller 44 generates a command signal(s) in response to the input signal for instructing one or both of the vibration producing apparatuses 28 and/or 30 to produce vibrations that are conducive for inducing drowsiness. In one example and as illustrated, the vibration producing apparatus 28 or 30 is a shaker actuator 32 or an audio speaker 34 and the command signal is communicated to the amplifier 52. The amplifier 52 produces a voltage and current in response to the command signal and the voltage and current are communicated to the shaker actuator 32 or the audio speaker 34 for producing the vibrations.

In another example and as illustrated, the vibration producing apparatus 28 or 30 is a motorized eccentric shaker 36 and the command signal is communicated to the motor control electronics 50. The motor control electronics 50 produces a motor voltage in response to the command signal and the motor voltage is communicated to the motorized eccentric shaker 36 for producing the vibrations.

Figure 9:
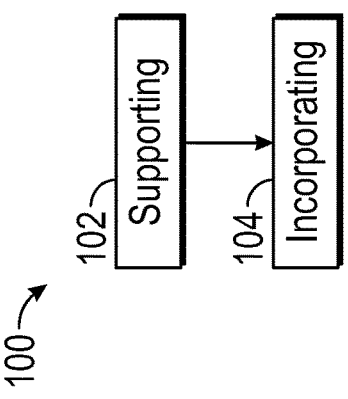
FIG. 9 illustrates a method for fabricating an aircraft seat assembly in accordance with an exemplary embodiment.

Referring to FIG. 9, a method 100 for fabricating an aircraft seat assembly is provided. The method 100 includes, at step 102, supporting a seat cushion with a seat structure. With continuing reference to FIGS. 1-8, in an embodiment, the seat structure may comprise seat frame 16 discussed above. At step 104, a vibration producing apparatus is incorporated into the aircraft seat assembly. The vibration producing apparatus is configured for producing vibrations conducive for inducing drowsiness. In some embodiments, the vibration producing apparatus may comprise vibration producing apparatuses 28 and/or 30, discussed above. Incorporating the vibration producing apparatus into the aircraft seat assembly includes disposing the vibration producing apparatus adjacent to and/or within the seat structure for transferring the vibrations to the seat occupant.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. An aircraft seat assembly for supporting a seat occupant, the aircraft seat assembly comprising:
    a seat structure;
    a seat cushion supported by the seat structure; and
    a vibration producing apparatus configured to produce vibrations, and wherein the vibration producing apparatus is disposed one of adjacent to and within the seat structure for transferring the vibrations to the seat occupant, wherein the seat structure includes a seat substructure that is configured to couple to a seat track, wherein the vibration producing apparatus is disposed within the seat substructure, and wherein the vibration producing apparatus is an audio speaker.

2. The aircraft seat assembly of claim 1, wherein the vibrations have a frequency of from about 1 to about 15 Hz.

3. The aircraft seat assembly of claim 1, wherein the vibrations have an amplitude of from about 0.005 inches to about 1 inch.

4. The aircraft seat assembly of claim 1, further comprising a controller in communication with the vibration producing apparatus and configured to receive an input signal and to generate a command signal in response to the input signal for instructing the vibration producing apparatus to produce the vibrations.

5. The aircraft seat assembly of claim 4, further comprising a control panel in communication with the controller and configured to receive an input from the seat occupant and to generate the input signal in response to the input.

6. The aircraft seat assembly of claim 4, wherein the controller is configured to receive the input signal from one of a mobile device and an onboard network.

7. The aircraft seat assembly of claim 4, further comprising an amplifier in communication with the controller and the vibration producing apparatus to receive the command signal and to produce a voltage and current in response to the command signal for communication to the vibration producing apparatus to produce the vibrations.

8. An aircraft seat assembly for supporting a seat occupant, the aircraft seat assembly comprising:
    a seat base portion including a seat base structure portion and a seat base cushion supported by the seat base structure portion;
    a seat backrest portion coupled to the seat base portion and configured to extend substantially upright from the seat base portion, wherein the seat backrest portion includes a seat backrest structure portion and a seat backrest cushion supported by the seat backrest structure portion; and
    a vibration producing apparatus configured to produce vibrations, and wherein the vibration producing apparatus is disposed one of adjacent to and within one of the seat base structure portion and the seat backrest structure portion for transferring the vibrations to the seat occupant, wherein the seat base structure portion includes a seat substructure that is configured to couple to a seat track, wherein the vibration producing apparatus is disposed within the seat substructure, and wherein the vibration producing apparatus is an audio speaker.

9. The aircraft seat assembly of claim 8, wherein the vibration producing apparatus is a first vibration producing apparatus configured to produce the vibration as first vibrations, and the aircraft seat assembly further comprises a second vibration producing apparatus configured to produce second vibrations conducive for inducing drowsiness, and wherein the second vibration producing apparatus is disposed one of adjacent to and within the seat backrest structure portion for transferring the second vibrations to the seat occupant.

10. The aircraft seat assembly of claim 9, wherein the second vibration producing apparatus is an additional audio speaker.

11. The aircraft seat assembly of claim 9, further comprising a controller in communication with the first and second vibration producing apparatuses and configured to receive an input signal and to generate a first command signal and a second command signal in response to the input signal, wherein the first command signal instructs the first vibration producing apparatus to produce the first vibrations and the second command signal instructs the second vibration producing apparatus to produce the second vibrations.

12. A method for fabricating an aircraft seat assembly for supporting a seat occupant, the method comprising the steps of:
supporting a seat cushion by a seat structure, wherein the seat structure includes a seat substructure that is configured to couple to a seat track; and
incorporating a vibration producing apparatus into the aircraft seat assembly, wherein incorporating the vibration producing apparatus includes disposing the vibration producing apparatus within the seat substructure for transferring the vibrations to the seat occupant, and wherein the vibration producing apparatus is an audio speaker.

* * * * *